United States Patent
Guo et al.

[11] Patent Number: 6,151,521
[45] Date of Patent: Nov. 21, 2000

[54] MEDICAL SUPPORT SYSTEM

[75] Inventors: Qinglian Guo; Mieko Ohsuga; Katsuyuki Kamei; Katsunobu Muroi; Mitsuo Maeda, all of Tokyo, Japan

[73] Assignee: Mitsubishi Denki Kabushiki Kaisha, Tokyo, Japan

[21] Appl. No.: 09/071,831

[22] Filed: May 4, 1998

[30] Foreign Application Priority Data

Nov. 19, 1997 [JP] Japan .................................. 9-318147

[51] Int. Cl.$^7$ ...................................................... A61B 5/00
[52] U.S. Cl. .................... 600/407; 128/904; 128/905; 128/922; 345/2; 348/14; 396/325
[58] Field of Search ............................ 600/407; 128/903, 128/904, 905, 922; 382/128; 396/333, 14, 325; 345/1, 2, 903; 348/13, 14, 15, 7, 12, 36, 38, 39

[56] References Cited

U.S. PATENT DOCUMENTS

| 4,922,909 | 5/1990 | Little et al. ............................... 128/630 |
| 5,544,649 | 8/1996 | David et al. ............................... 128/630 |
| 5,619,995 | 4/1997 | Lobodzinski .......................... 128/653.1 |
| 5,631,973 | 5/1997 | Green ...................................... 382/128 |
| 5,701,904 | 12/1997 | Simmons et al. ........................ 128/670 |
| 5,805,117 | 9/1998 | Mazurek et al. ............................. 345/1 |
| 5,941,829 | 8/1999 | Saltzstein et al. ....................... 600/509 |

FOREIGN PATENT DOCUMENTS

| 0505627 | 9/1992 | European Pat. Off. . |
| 2218336 | 8/1990 | Japan . |
| 4336677 | 11/1992 | Japan . |
| 8215158 | 8/1996 | Japan . |
| 975404 | 3/1997 | Japan . |
| 9117417 | 5/1997 | Japan . |

Primary Examiner—Marvin M. Lateef
Assistant Examiner—Eleni Mantis Mercader
Attorney, Agent, or Firm—Leydig, Voit & Mayer, Ltd.

[57] ABSTRACT

A medical support system includes a patient-side system including patient shooting devices for photographing a patient's body and forming respective images displaying respective parts of the patient's body; a medical-side system located at a position spaced away from the patient-side system and including an image synthesizer for splicing together, at boundary portions, respective adjacent images of the patient's body to produce a composite image displaying an area of the patient's body extending across the respective images, and a display for displaying the composite image produced by the image synthesizer; and a communication link for transmitting information between the medical-side system and the patient-side system and for transferring the images produced by the patient shooting devices to the medical-side system.

20 Claims, 15 Drawing Sheets

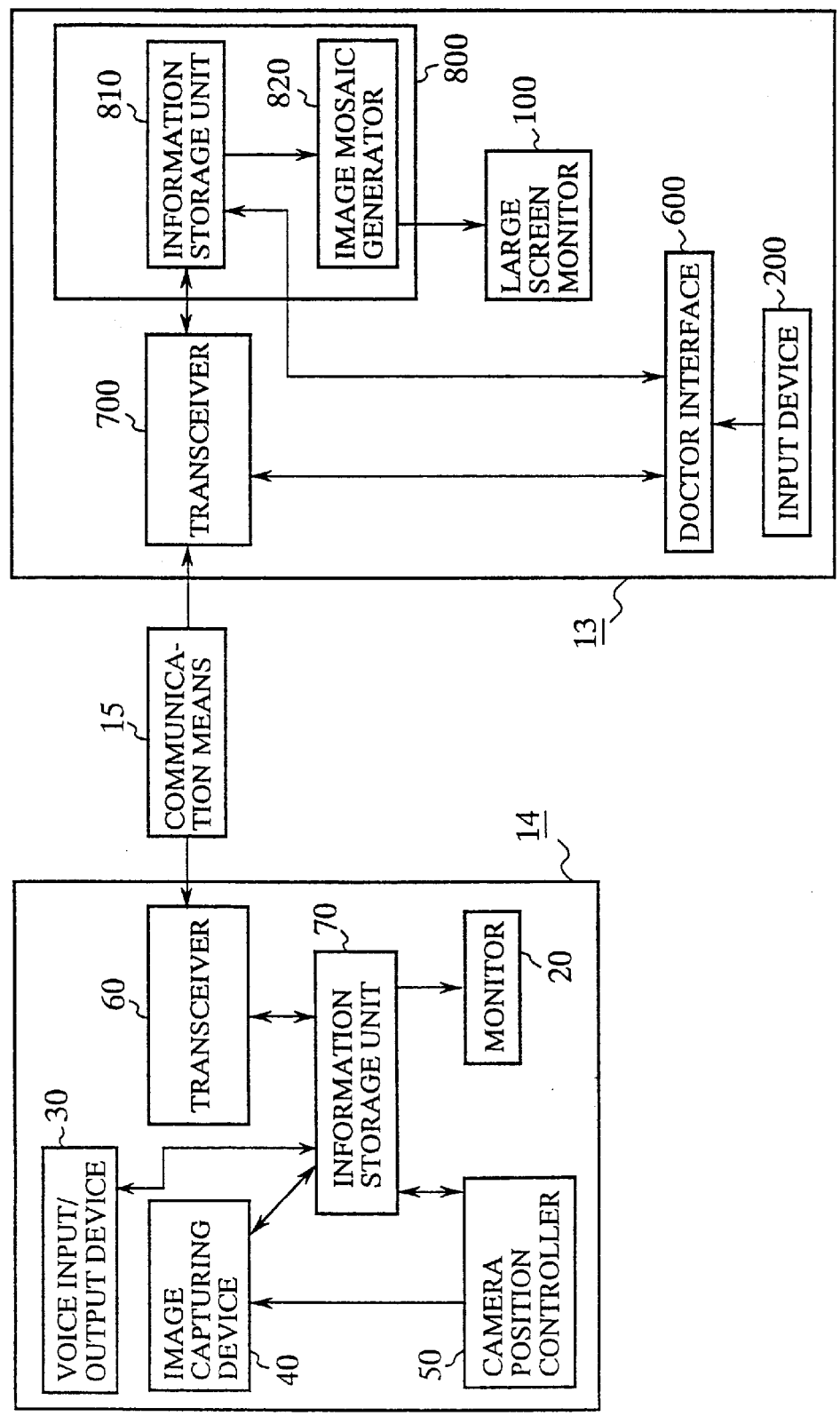

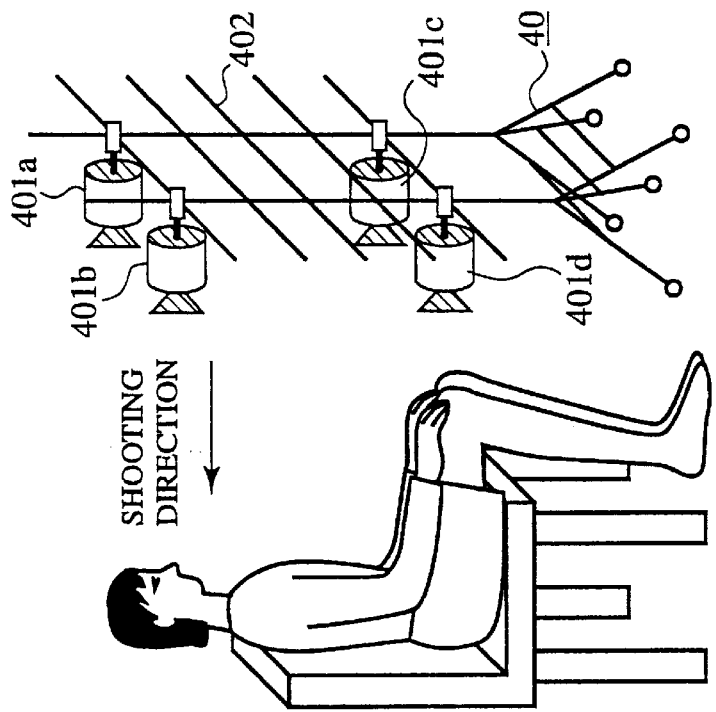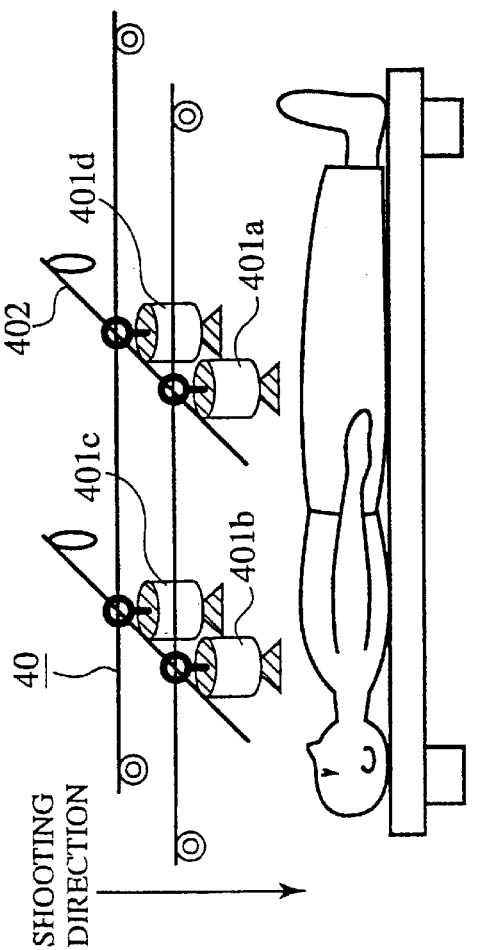
FIG.2(a)
FIG.2(b)

RADIUS OF CAMERA r

FRONT DORSALPOSITION

SIDE DORSALPOSITION

FRONT SEATING POSITION

SIDE SEATING POSITION

EXAMINED-PART SELECTION

CAMERA POSITION DISPLAY (ON)

EXAMINED-RANGE SELECTION

CAMERA POSITION SELECTION

FIG.8

| | | PART NUMBER | PART NAME | PART VOICE INFORMATION | CORRESPONDING CAMERA NUMBER (SHOOTING POSTURE) |
|---|---|---|---|---|---|
| FRONT DORSAL-POSITION | PART SELECTION | 1 | 2 | 3+6 | 5 |
| | CAMERA | C | C | C | B+C |
| SIDE DORSAL-POSITION | | | | | |
| | | | | | |
| FRONT SEATING POSITION | | | | | |
| | | | | | |
| SIDE SEATING POSITION | | | | | |
| | | | | | |

ELLIPTICAL CONE PROJECTED PLANE

MEDICAL SUPPORT SYSTEM

BACKGROUND OF THE INVENTION

1. Field of the Invention

The present invention relates to a medical support system for supporting medical treatments to be put on a patient located in a distant place by a medical treater or conductor, and particularly to an at-home medical treatment support system wherein image information and voice information are transferred between medical treaters placed in distant positions or between a medical treater and a patient through a communication media such as a communication network, a medical support vehicle capable of satellite communications, or the like to thereby allow medical treatments while better mutual understanding is being established between the patient and the medical treater.

2. Description of the Prior Art

Attention has recently been focused on a medical support system for connecting between a patient's home and a distant hospital at which a medical conductor or treater such as a doctor or the like is permanently stationed, through a communication media such as a communication network, satellite communications or the like to perform image communications, thereby allowing the doctor to diagnose a disease of a patient located in a distant place and make his/her health consultation or the like. There have been proposed, for example, a medical image information transmission system disclosed in JP-A No. 2-218336, a remote-medical system disclosed in JP-A No. 9-75404, a medical support system using satellite communication functions, disclosed in JP-A No. 8-215158, etc.

In such conventionally-proposed medical support systems, a male or female nurse calls at patient homes with a portable television conference unit capable of making a loop type multipoint conference and a portable medical device unit and transmits, in real time, medical data about a plurality of patients located in distant places, using a satellite communication network and a ground communication network via a traveling medical support vehicle capable of satellite communications. On the other hand, a medical conductor or treater in a distant hospital analyzes the received data and examines a patient while speaking with a medical treater and the patient located in a distant place through bidirectional communications using images and voices. The patient medical data is transmitted to a plurality of medical treaters located in distant places and the medical treaters in the remote locations examine the patient while bidirectionally speaking or interacting with the patient through images and voices using television conference functions. As a result, the plurality of medical treaters in different locations can examine one patient simultaneously.

Further, a patient monitor system disclosed in JP-A No. 4-327832 performs a two-way communication using physiological data and patient video images and voices through a communication network. The hospital side has the function of receiving the combined video images and physiological data together and displaying them on a display, and reproducing the voices and transmitting voice data to the patient side and is thereby capable of examining a patient in a remote location.

Moreover, a pathology remote image diagnostic system disclosed in JP-A No. 9-117417 has also the same function as described above. A pathological specialist located away from a hospital and the hospital are connected to one another through a communication network so that tissue images under a microscope are transferred to the pathological specialist side. Thereafter, the pathological specialist performs pathological examinations and diagnostics, based on the tissue images displayed on a terminal provided on the pathological specialist side and immediately transfers the result of diagnosis thereof to the hospital side.

However, problems exist which are not capable of being solved by the conventionally-proposed arts. Since the patient and the medical treater do not directly look at each other under the construction of the prior art, how to transmit clear and accurate patient motion pictures to the medical treater side grows in importance. In the prior arts, a method of capturing patient motion pictures by a single video camera is commonly used. However, since it is necessary to shorten the distance between the patient and the video camera when one attempts to display images high in accuracy, a problem arises in that an image corresponding to the whole body of the patient cannot be captured. If one attempts to shoot or photograph the image of the whole body of the patient when one video camera for photographing the images of the patient is used, it is then necessary to increase the distance between the video camera and the patient. Therefore, a problem arises in that image resolution is scaled down. When only such an image scaled down in resolution or an image narrow in visual field is transmitted, this will result in the transmission of only information much less than practical, thus causing a problem for medical examination and care.

SUMMARY OF THE INVENTION

With the foregoing in view, it is therefore an object of the present invention to provide a medical support system capable of providing a medical treater with images wide in vidual field and high in resolution.

According to a first aspect of this invention, for achieving the above object, there is provided a medical support system comprising:

a medical-side system having image synthesizing means for splicing neighborhoods of boundary portions of a plurality of images together to produce one composite image and display means for displaying the composite image produced from the image synthesizing means;

a patient-side system provided at a position spaced away from the medical-side system and having patient image shooting means for photographing a patient's body using a plurality of shooting devices; and communication means capable of transmitting information sent from the medical-side system and information sent from the patient-side system in either direction between the medical-side system and the patient-side system and for transferring a plurality of pieces of image information obtained by the patient image shooting means of the patient-side system to the medical-side system. Thus, medical treatments can be done with efficiency.

According to a second aspect of this invention, there is provided a medical support system wherein a medical-side system has shooting-device position control means for controlling the positions of a plurality of shooting devices of patient image shooting means in a patient-side system. It is thus possible to easily obtain images of patient parts, which are required on the medical system side.

According to a third aspect of this invention, there is provided a medical support system wherein a medical-side system has shooting-device position display means for displaying the positions of a plurality of shooting devices thereon. Thus, the medical-side system can easily handle the positions of the shooting devices and easily control the shooting devices.

According to a fourth aspect of this invention, there is provided a medical support system wherein a medical-side system has means for selecting a patient part/range photographed by a patient-side system and shooting-device position control means controls patient image shooting means according to the information selected by the selecting means. Thus, the shooting devices can be easily controlled.

According to a fifth aspect of this invention, there is provided a medical support system wherein a medical-side system has human-body form image display means for displaying a human-body form image corresponding to the form of a human body and displaying a part of the human-body form image corresponding to a patient part selected by selecting means in distinction from other parts. Thus, the medical-side system can easily recognize which part of the patient would be photographed.

According to a sixth aspect of this invention, there is provided a medical support system wherein a medical-side system has shot-state input means for selecting and inputting a photographed posture of a patient and human-body form image display means displays thereon a human-body form image corresponding to the posture inputted to the shot-state input means. Thus, images corresponding to various patient's postures can be easily photographed.

According to a seventh aspect of this invention, there is provided a medical support system wherein a medical-side system includes voice input means for inputting a voice, voice output means for outputting voice information sent from a patient-side system and shooting means for photographing images, and the patient-side system includes display means for displaying the images obtained by the shooting means of the medical-side system and voice ad output means for outputting the voice inputted from the voice input means of the medical-side system. Thus, voice information and image information can be transmitted in either direction.

According to an eighth aspect of this invention, there is provided a medical support system wherein a medical-side system has voice information recognizing means for recognizing information about a voice inputted from voice input means and outputting a signal for specifying a human body part to be photographed. Thus, shooting devices can be easily controlled.

According to a ninth aspect of this invention, there is provided a medical support system wherein a plurality of shooting devices of a patient-side system are placed on the same plane. Thus, a plurality of images obtained from a plurality of shooting devices can be easily combined into one.

According to a tenth aspect of this invention, there is provided a medical support system wherein a plurality of shooting devices are respectively movable within one plane. Thus, a specific affected part of a patient can be photographed with it as the center.

According to an eleventh aspect of this invention, there is provided a medical support system wherein a plurality of shooting devices are placed so as to differ from each other in their shooting directions. Thus, patient's three-dimensional images can be obtained and hence larger pieces of information about the patient can be acquired.

According to a twelfth aspect of this invention, there is provided a medical support system wherein a medical-side system has shooting-device position calculating means for calculating the position of each shooting device of a patient-side system and the shooting-device position calculating means calculates the positions of the plurality of shooting devices so that the amounts of movements of the plurality of shooting devices reach the minimum or the number of the plurality of shooting devices reaches the minimum. Thus, the time required to shift each shooting device becomes short. Alternatively, the time required to transfer the image photographed by the corresponding shooting device becomes short.

According to a thirteenth aspect of this invention, there is provided a medical support system wherein a patient-side system has first information storing means for storing therein images of a patient photographed by patient image shooting means every shooting times and a medical-side system has second information storing means for storing therein the images sent from the patient-side system every shooting times. It is thus possible to easily take out the image information about the patient photographed in the past.

According to a fourteenth aspect of this invention, there is provided a medical support system wherein image synthesizing means includes means for determining a layout of a plurality of images from information about the positions of a plurality of shooting devices, means for extracting boundaries of the plurality of images through a boundary extracting filter, means for calculating a center line of an area which overlaps with images adjacent to each other in the vicinities of the boundaries of the respective images, means for calculating intersections of the boundaries extracted from the boundary extracting means and the adjacent images and extracting an area in which the intersections increase, thereby producing a template image, means for creating a window identical in size to the template image and calculating a position used to splice the adjacent images together while moving the window within the overlapping area, registration processing means for adjusting a mutually-related position of the adjacent images in the vertical or horizontal direction and effecting a registration process on the adjacent images so that the boundaries of the adjacent images are joined to each other, and means for effecting a blending process on intensities or color tones of the center line and pixels around the center line. Thus, the vicinities of the boundaries at the time that the images are joined to each other, can be smoothly spliced.

According to a fifteenth aspect of this invention, there is provided a medical support system wherein a intensity blending process executing means calculates the densities of respective pixels within an area which overlaps with adjacent images, from the following equations (1) through (3):

$$I(p) = I1(p) \times s1(p) + I2(p) \times s2(p) \tag{1}$$

$$s1(p) = -1.0 \times (x1 - R + d)/d + 1.0 \tag{2}$$

$$s2(p) = 1.0 \times (x2 + R - d)/d + 1.0 \tag{3}$$

where p: the position of each pixel that belongs to the overlapping area,
wherein the position of p represented in the form of a coordinate system of one image is given as (x1, y1) and the position of p represented in the form of a coordinate system of the other image is given as (x2, y2),
I(p): the density of a pixel at the point p of a composite image,
I1(p): the density of a pixel at the point p of one image,
I2(p): the density of a pixel at the point p of the other image,
R: the radius of an image area, and
d: the width of the overlapping area.

Thus, variations in intensity in the vicinities of the boundaries at the time that the images are spliced together, can be spliced smoothly.

According to a sixteenth aspect of this invention, there is provided a medical support system wherein a color tone blending process executing means calculates the densities of respective pixels within an area which overlaps with adjacent images, from the following equations (4) through (8):

$$R(p)=R1(p) \times s1(p)+R2(p) \times s2(p) \quad (4)$$

$$G(p)=G1(p) \times s1(p)+G2(p) \times s2(p) \quad (5)$$

$$B(p)=B1(p) \times s1(p)+B2(p) \times s2(p) \quad (6)$$

$$s1(p)=-1.0 \times (x1-R+d)/d+1.0 \quad (7)$$

$$s2(p)=1.0 \times (x2+R-d)/d+1.0 \quad (8)$$

where p: the position of each pixel that belongs to the overlapping area, wherein the position of p represented in the form of a coordinate system of one image is given as (x1, y1) and the position of p represented in the form of a coordinate system of the other image is given as (x2, y2), R(p), G(p) and B(p): tonal values of respective colors of R (red), G (green) and B (blue) of a pixel at a point p of a composite image, R1(p), G1(p) and B1(p): tonal values of respective colors of R (red), G (green) and B (blue) of a pixel at the point p of one image, R2(p), G2(p) and B2(p): tonal values of respective colors of R (red), G (green) and B (blue) of a pixel at the point p of the other image, R: the radius of an image area, and d: the width of the overlapping area.

Thus, variations in color tone in the vicinities of the boundaries at the time that the images are joined to each other, can be smoothly spliced together.

According to a seventeenth aspect of this invention, there is provided a medical support system wherein a predetermined background pattern is provided and a plurality of shooting devices photograph a patient body with the predetermined background pattern as the background. Thus, images can be spliced together with further precision.

According to an eighteenth aspect of this invention, there is provided a medical support system wherein a predetermined background pattern is configured so that straight lines are placed along a predetermined direction. Thus, images can be spliced together with further precision.

According to a nineteenth aspect of this invention, there is provided a medical support system wherein a predetermined background pattern is configured so that the widths of straight lines are varied along a predetermined direction. Thus, images can be spliced together with further precision.

According to a twentieth aspect of this invention, there is provided a medical support system wherein a predetermined background pattern is configured so that spaces between adjacent straight lines are varied along a predetermined direction. Thus, images can be spliced together with further precision.

BRIEF DESCRIPTION OF THE DRAWINGS

Other objects and advantages of the present invention will be more completely understood from the following detailed description, taken in conjunction with the accompanying drawings wherein:

FIG. 1 is a diagram showing a configuration of a medical support system according to a first embodiment (First Embodiment) of the present invention;

FIGS. 2(a) and 2(b) are respectively diagrams illustrating a configuration of an image capturing device of the medical support system shown in FIG. 1;

FIG. 8 is a diagram showing one example of results obtained by calculating the positions of the video cameras of the image capturing device of the medical support system shown in FIG. 1;

DETAILED DESCRIPTION OF THE PREFERRED EMBODIMENTS

Figure 3A:
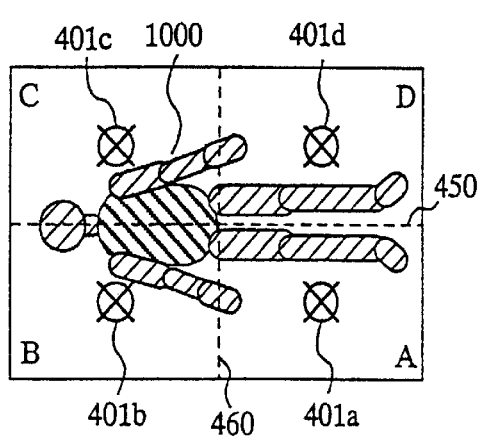
FIGS. 3(a), 3(b), 3(c) and 3(d) are respectively diagrams for describing operations of a plurality of video cameras of the image capturing device of the medical support system shown in FIG. 1.
Figure 3B:
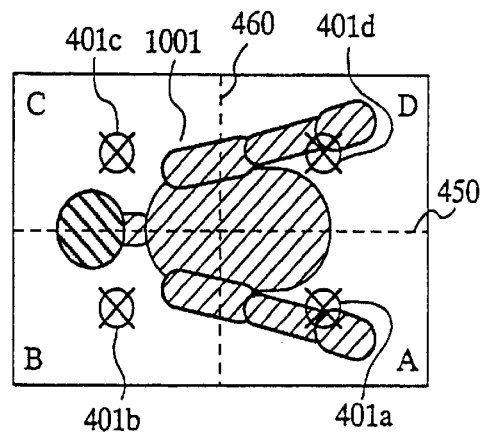
Figure 3C:
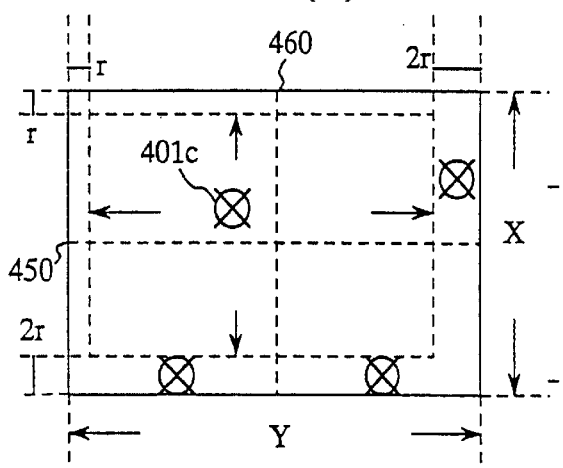
Figure 3D:
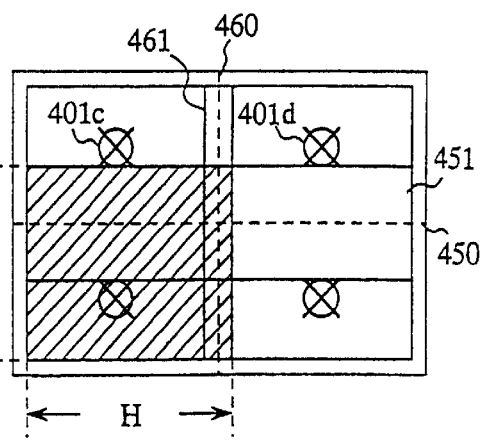

Preferred embodiments of the present invention will hereinafter be described in detail with reference to the accompanying drawings.

First Embodiment

FIG. 1 is a block diagram showing a medical support system according to the present first embodiment. In the drawing, reference numeral 13 indicates a medical-side system for causing a medical conductor or treater such as a doctor or a male or female nurse or the like to recognize a state of a patient and transferring information from the medical treater to the patient. Reference numeral 14 indicates a patient-side system for photographing or shooting the patient, transferring the result of photography to the medical-side system 13 and receiving information transmitted from the medical-side system 13. Reference numeral 15 indicates a means of communication for performing the transfer of information between the medical-side system 13 and the patient-side system 14. A communication line or network for bidirectionally transmitting information, such as an ISDN, a communication satellite or the like is used as the communication means 15.

The medical-side system 13 and the patient-side system 14 are provided at locations spaced away from each other. The medical-side system 13 is located in a hospital or the like, for example, whereas the patient-side system 14 is located in a patient house or a hospital different from that provided with the medical-side system 13. The medical-side system 13 and patient-side system 14 placed at the remote sites transmit and receive information (image information or voice or speech information) bidirectionally or in either direction through the communication means 15.

In the patient-side system 14, reference numeral 60 indicates a transceiver or transmitter-receiver for receiving therein information sent from the medical-side system 13 and transmitting information obtained from the patient-side system 14 to the medical-side system 13. Reference numeral 70 indicates an information storage unit which serves as a first information storing means, for storing therein the information received from the transceiver 60 and the information obtained from the patient-side system 14. The information storage unit 70 may include a RAM, a hard disc or the like, for example, and holds therein information such as speech information, image information, information about camera positions, etc. Reference numeral 20 indicates a monitor, which serves as a display means for displaying the image information sent from the medical-side system 13 thereon. Reference numeral 30 indicates a voice input/output device for outputting information about the voice of the medical treater, which is sent from the medical-side system 13 and inputting information about the voice of a patient or an operator of the patient-side system 14, which is to be transmitted from the patient-side system 14 to the medical-side system 13, to the patient-side system 14. Reference numeral 40 indicates an image capturing device corresponding to a patient image shooting or sensing means for shooting the patient. The image capturing device 40 has a plurality of photographing or shooting devices. In the present first embodiment, the image capturing device 40 uses video cameras as the shooting devices. The number of the video cameras is four. Reference numeral 50 indicates a camera position controller corresponding to a shooting-device position control means for controlling the positions of the plurality of shooting devices. The camera position controller 50 calculates a shooting position of each video camera so that a certain part of a patient can be photographed when the medical treater needs a picture or image about the certain part of the patient through the medical-side system 13, and shifts the video camera to the calculated position. The patient-side system 14 comprises the above-described monitor 20, voice input/output device 30, image capturing device 40, camera position controller 50 and transceiver 60.

In the medical-side system 13, reference numeral 700 indicates a transmitter-receiver or transceiver for transmitting information to be sent to the patient-side system 14 and receiving therein information sent from the patient-side system 14. Reference numeral 800 indicates a digital mosaic processor corresponding to an image synthesizing means for splicing the neighborhoods of boundary portions of a plurality of pictures or images captured from the video cameras of the image capturing device 40 in the patient-side system 14 to produce a composite image. The digital mosaic processor 800 includes an information storage unit 810 corresponding to a second information storing means for storing therein information sent to the transceiver 700 from the patient-side system 14 and information to be transmitted from the medical-side system 13 to the patient-side system 14, and an image mosaic generator 820 for synthesizing or merging a plurality of images sent from the patient-side system 14 into one. Reference numeral 100 indicates a large screen monitor corresponding to a display means for displaying the image synthesized by the digital mosaic processor 800 thereon. The large screen monitor 100 has a screen having a size capable of displaying, for example, a whole-body image of a patient in a substantially life-sized form. The display screen of the large screen monitor 100 is a multi-screen configured one having ultra-high resolution. Reference numeral 200 indicates an input device corresponding to an input means for inputting information. As the input device 200, a mouse, a joystick, a keyboard, a voice input microphone or the like may be included. Reference numeral 600 indicates a doctor interface corresponding to an input supporting means provided so as to allow the medical treater to input necessary information with efficiency. A selecting means comprises the input device 200 and the doctor interface 600.

FIGS. 2(*a*) and 2(*b*) are respectively diagrams showing one example of a specific configuration of the image capturing device 40. FIG. 2(*a*) illustrates a configuration in which an image of a patient assuming the posture of the dorsal decubitus or dorsal position at which the patient lies face up, is captured. FIG. 2(*b*) shows a configuration in which an image of a patient assuming the posture of the seating position at which the patient sits on a chair, is captured.

Referring to FIGS. 2(*a*) and 2(*b*), reference numerals 401*a*, 401*b*, 401*c* and 401*d* indicate video cameras respectively. These video cameras 401*a* through 401*d* are respectively spaced predetermined intervals away from each other and placed in their corresponding positions close to the patient. It is thus possible to finely take images or pictures of the patient. Further, the use of ones having high-resolution as the video cameras 401*a* through 401*d* permits more precise image photography. Reference numeral 402 indicates a lattice network. The video cameras 401*a* through 401*d* can move on the lattice network 402 under the action of a drive means (not shown) and can photograph after they have stopped at lattice points of the lattice network 402. The lattice network 402 is provided on the same horizontal plane (see FIG. 2(*a*)) or vertical plane (see FIG. 2(*b*)) orthogonal to the direction of patient's eyes. Therefore, the video cameras 401*a* through 401*d* are located on the same horizontal or vertical plane orthogonal to the direction of patient's eyes. Thus, when the patient is shot by the use of the video cameras 401*a* through 401*d*, shooting conditions (shooting distances in particular) between the respective video cameras and the patient become equal to each other. Therefore, a process for synthesizing the images by the digital mosaic processor 800, which is capable of eliminating the need for enlargement/reduction of any of the captured images upon merging the captured images into one, is simplified.

FIGS. 3(*a*) through 3(*d*) are diagrams for describing the relationship of placement between the video cameras 401*a* through 401*d* constituting the image capturing device 40 and shooting ranges of the video cameras 401*a* through 401*d*. In the drawing, designated at numerals 1000 and 1001 are diagrams typically showing patient's bodies respectively. Now consider that the shooting range of the image capturing device 40 lies within an area represented in the form of a rectangle having a short side indicated by X and a long side indicated by Y as shown in FIG. 3(*c*). Further, the above-described rectangle is further divided into four rectangles (corresponding to areas A, B, C and D shown in FIGS. 3(*a*) and 3(*b*)). These areas will be defined as respective principal shooting ranges for the video cameras 401*a* through 401*d*. Reference numerals 450 and 460 indicate boundaries between the rectangles A, B, C and D respectively. Reference numerals 451 and 461 respectively indicate areas where the shooting ranges for the video cameras 401*a* through 401*d* overlap. Although the video cameras 401*a* through 401*d* can move on the lattice network 402, the maximum movable ranges of the respective video cameras, e.g., the maximum movable range of the video camera 401*c* as an example is limited to within an area constituting a rectangle having a length of Y-3r extending in the direction of its long side and a length of X-3r extending in the direction of its short side. The shooting ranges of the video cameras 401*a* through 401*d* are identical in size to each other, and correspond to square areas whose individual sides are H (where H will be defined so as to satisfy conditions of X>H>X/2 or Y>H>Y/2).

Figure 4:
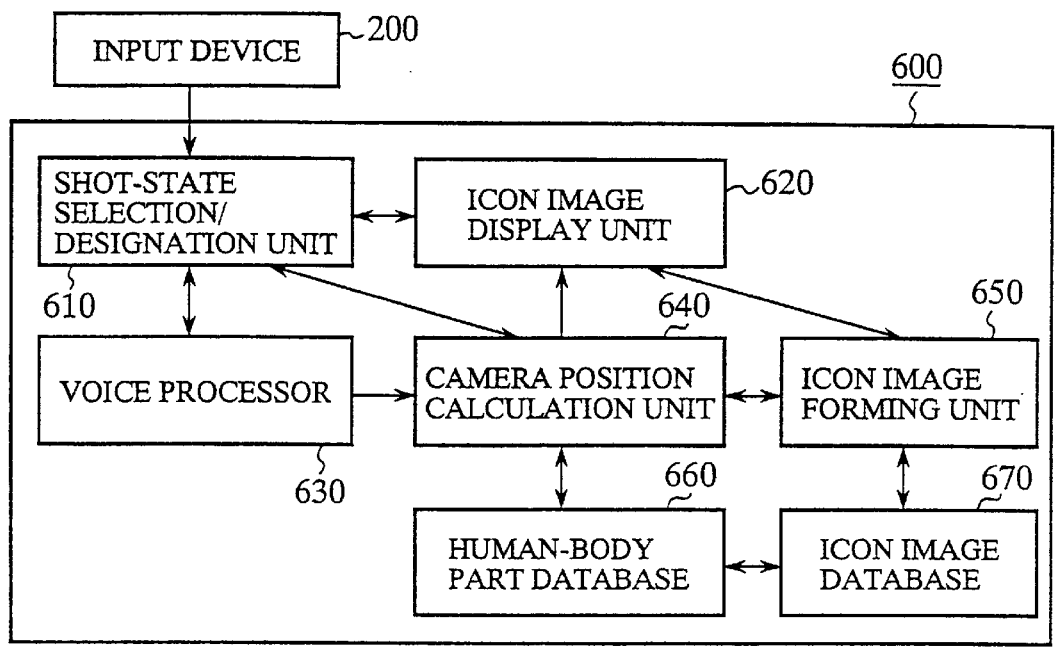
FIG. 4 is a diagram depicting a configuration of a doctor interface employed in the medical support system shown in FIG. 1.

FIG. 4 is a block diagram showing a specific configuration of the doctor interface 600. In the drawing, reference numeral 610 indicates a shot-state selection/designation unit for selecting/setting a part/range to be examined and diagnosed from information inputted from the input device 200. Reference numeral 620 indicates an icon image display unit for displaying an image corresponding to the shot state of a patient in the form of an icon image to provide easy understanding of the medical treater. Reference numeral 630 indicates a speech or voice processor for, when the part to be examined and diagnosed by the medical treater is specified or designated by his/her voice, recognizing information about its voice. Reference numeral 640 indicates a camera position calculation unit corresponding to a shooting-device position calculating means for calculating the positions of the video cameras 401*a* through 401*d* of the image capturing device 40 according to information (called "shot-state selected/designated information") selected/designated by the shot-state selection/designation unit 610. Reference numeral 650 indicates an icon image forming unit for producing each of icon images that reflect shot states at respective points in time, based on information (called "camera position information") about the positions of the video cameras 401*a* through 401*d*, the shot-state selected/designated information, an icon image database of the system, etc. The icon image formed by the icon image forming unit 650 is sent to the icon image display unit 620 where it is displayed thereon. Reference numeral 660 indicates a human-body part database for storing therein information about respective parts or regions of a human body. Reference numeral 670 indicates an icon image database for storing information about the icon images therein.

A medical treater placed in the medical-side system 13 remote-controls the patient-side system 14 placed in the distant location through the doctor interface 600 to thereby operate the medical-side system 13 so as to bring an image desired to be observed or viewed by the medical treater therein.

Figure 5:
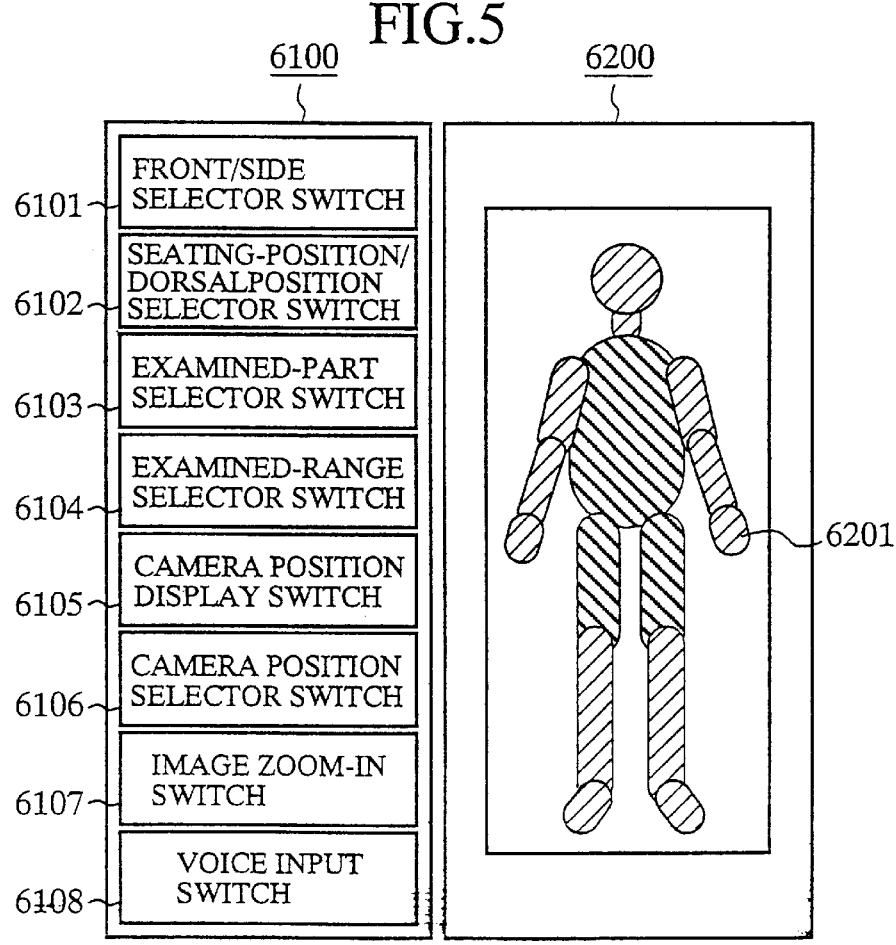
FIG. 5 is a diagram showing one example of a screen displayed on the doctor interface of the medical support system shown in FIG. 1.
Figure 6A:
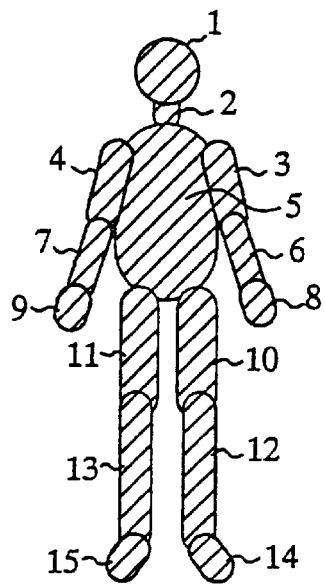
FIGS. 6(a), 6(b), 6(c) and 6(d) are respectively diagrams showing examples of screens displayed on the doctor interface of the medical support system shown in FIG. 1.
Figure 6B:
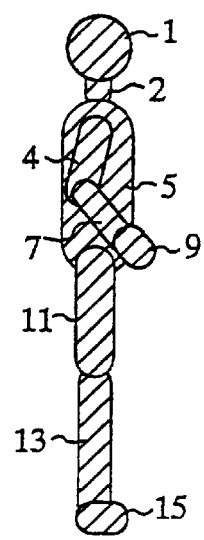
Figure 6C:
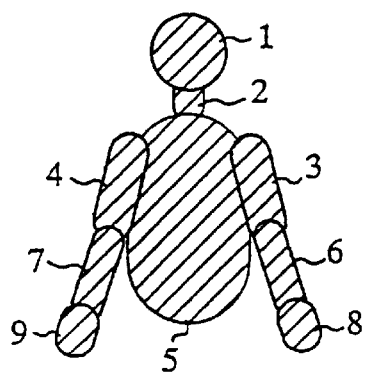
Figure 6D:
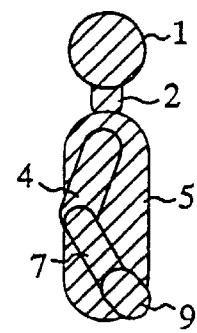
Figure 7A:
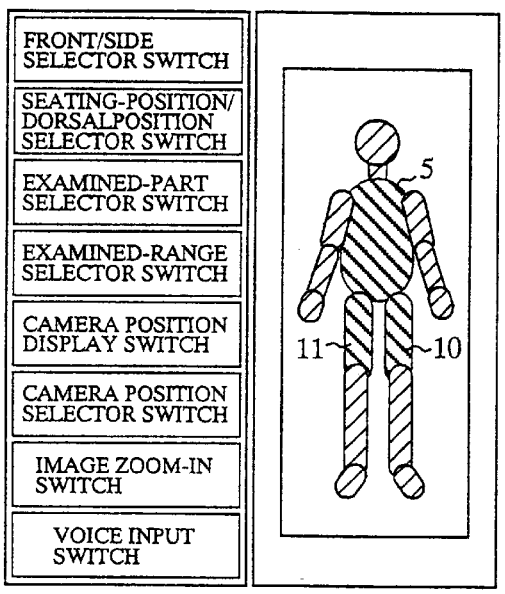
FIGS. 7(a), 7(b), 7(c) and 7(d) are respectively diagrams illustrating examples of screens displayed on the doctor interface of the medical support system shown in FIG. 1.
Figure 7B:
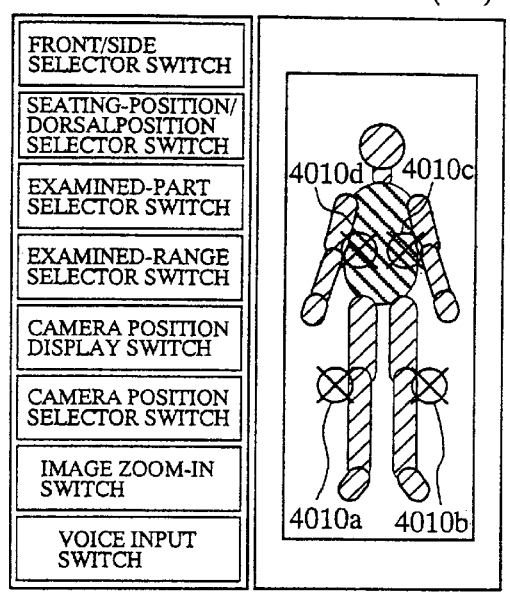
Figure 7C:
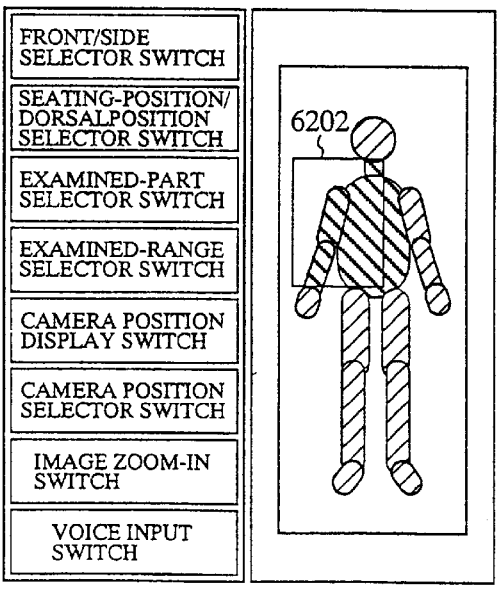
Figure 7D:
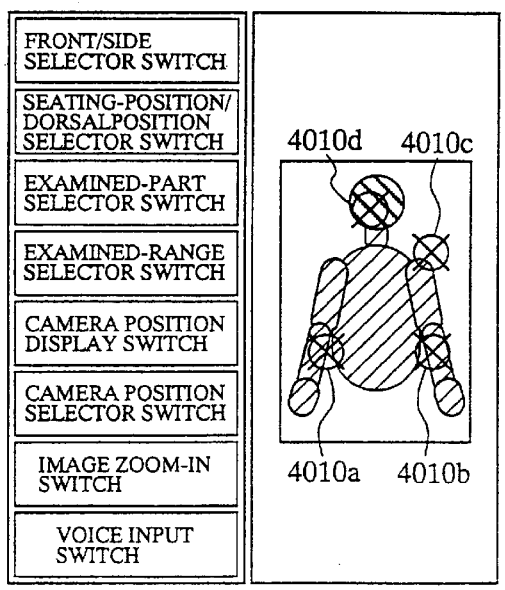

FIG. 5 is a diagram showing examples of a displayed screen of the shot-state selection/designation unit 610 and a displayed screen of the icon image display unit 620. In the drawing, reference numeral 6100 indicates the displayed screen of the shot-state selection/designation unit 610. The displayed screen 6100 includes a front/side selector switch 6101 for selecting either the front or side direction of a patient to be shot or photographed and displaying it, a seating-position/dorsalposition selector switch 6102 for selecting either a posture of the order of seat of a patient to be shot or a posture of the dorsal position thereof, an examined-part selector switch 6103 for selecting and designating or specifying a part of the patient to be examined, an examined-range selector switch 6104 for allowing a medical conductor or treater to select and specify a range to be examined, a camera position display switch 6105 for bringing the positions of the video cameras 401*a* through 401*d* into icons and displaying them, a camera position selector switch 6106 for selecting and moving the video cameras displayed in the form of the icons when the camera position display switch 6105 is turned on, to thereby shift the specified video cameras 401*a* through 401*d*, an image zoom-in switch 6107 for allowing zooming in on an image of a shot patient, and a voice input switch 6108 for allowing a voice input.

Reference numeral 6200 indicates a screen displayed by the icon image display unit 620. Reference numeral 6201 indicates an human-body icon image displayed by typically bringing a human body into icon form. The human-body icon image 6201 is configured by dividing the human body into a plurality of parts and displaying them in combination.

The displayed screens 6100 and 6200 are displayed by displayers (not shown) for displaying them thereon. The medical treater can view or observe the displayed screens 6100 and 6200 through the screens of the displayers.

FIGS. 6(*a*) through 6(*d*) are respectively diagrams showing specific examples of the human-body icon image 6201. As shown in the drawing, these human-body icon images 6210 are diagrams showing the front (see FIG. 6(*a*)) and side (see FIG. 6(*b*)) of a patient at the time that the posture of the patient at its shooting is placed in a dorsal position, and the front (see FIG. 6(*c*)) and side (see FIG. 6(*d*)) at the time that the posture thereof is placed in a position sitting on a chair. These human-body icon images are suitably switched according to the information obtained from the front/side selector switch 6101 and the seating-position/dorsalposition selector switch 6102. In FIG. 6(*a*), for example, the human body is divided into fifteen regions or parts (such as the head 1, neck 2, left-upper arm 3, right-upper arm 4, body 5, left-lower arm 6, right-lower arm 7, left hand 8, right hand 9, left thigh 10, right thigh 11, left knee 12, right knee 13, left foot 14 and right foot 15). Further, patterns or colors are marked or displayed on these respective parts in combination. The colors or patterns marked on the respective parts are varied according to the selection from the displayed screen 6100.

These human-body icon images are all stored in the icon image database 670. The icon image forming unit 650 makes a combination of images produced from the icon image database 670 based on the camera positions and shot or photographed postures at respective points in time to produce each of icon images that reflect the shot states at that time and allow the icon images to be displayed on the display screen of the icon image display unit 620.

The doctor interface 600 has the following five functions as functions to specify or designate a patient's part/range necessary for the examination and diagnosis by the medical treater.

1. Function of turning on the examined-part selector switch 6103 to thereby select at least one part that constitutes the human-body icon image 6201 on the displayed screen 6200.

Selected parts (such as the body 5, left thigh 10 and right thigh 11) are displayed by colors or patterns different from those for the other parts (see FIG. 7(*a*)). Although the color of a pre-selection part was green, for example, it turns into red after the part's selection has been made. Thus, the part varies in pattern prior and posterior to the part's selection.

2. Function of turning on the examined-range selector switch 6104 to thereby specify a window 6202 having an area that one is desired to see on the displayed screen 6200, using the input device 200.

Assuming that parts contained in the designated window 6202 have been selected, their colors or patterns vary (see FIG. 7(*c*)).

3. Function of turning on the camera position display switch 6105 to thereby display camera icons 4010*a*, 4010*b*, 4010*c* and 4010*d* (see FIG. 7(*b*)).

At this time, the positions of the camera icons 4010*a* through 4010*d* are displayed so as to correspond to the positions of the video cameras 401*a* through 401*d* respectively.

4. Function of turning on the camera position display switch 6105 and turning on the camera position selector switch 6106 to thereby select the camera icons 4010*a* through 4010*d* displayed on the displayed screen 6200 and shift the same.

The selected camera icons 4010*a* through 4010*d* are shifted or animated to thereby calculate their corresponding shifted positions of the icons by the camera position calculation unit 640. Thereafter, such information is set to the patient-side system 14 to move the video cameras 401*a* through 401*d* (see FIG. 7(*d*)). As a result, the medical-side system 13 is capable of easily controlling the positions of the video cameras 401*a* through 401*d* of the patient-side system 14.

5. Function of turning on the voice input switch 6108 to thereby input the voice.

When a number and a name that one or medical treater desires to see, are inputted through his/her voice, the voice processor 630 recognizes the input voice information and performs a choice of a patient's part, posture and shooting direction and a choice and shift of the camera icons according to the recognized information.

The camera position calculation unit 640 automatically calculates the shooting positions of the respective video cameras 401*a* through 401*d* of the image capturing device 40 according to the choice by the shot-state selection/ designation unit 610 or the voice processor 630 (pieces of information about the positions of defaults for the respective video cameras have been stored in advance). The camera position calculation unit 640 calculates the positions of the video cameras 401*a* through 401*d* on condition that the algorithm of the camera position calculation unit 640 is placed under the following three constraints.

(1) To ensure sufficient shooting ranges in consideration of differences between individuals (such as height, thickness of a trunk, an overall balance in body, etc.)

(2) To minimize the amount of movement of each camera (3) To minimize the number of cameras necessary for photography Described specifically, it is first calculated or determined from information about a selected patient's part which video camera would take or assume a shooting range to which the selected patient's part belongs. Since information about patient's parts and information about video cameras belonging to shooting ranges of the parts are stored in the human-body part database 660 as information in advance, the corresponding video camera to be used for photography is selected from the part information selected by retrieving the stored information. FIG. 8 is a table showing results obtained by retrieving and displaying corresponding video camera numbers by the camera position calculation unit 640 when the shooting direction of a patient is front and its posture is placed in the dorsal position, and the head 1, neck 2, left-upper arm 3, left-lower arm 6 and body 5 are selected as the human parts.

Figure 9A:
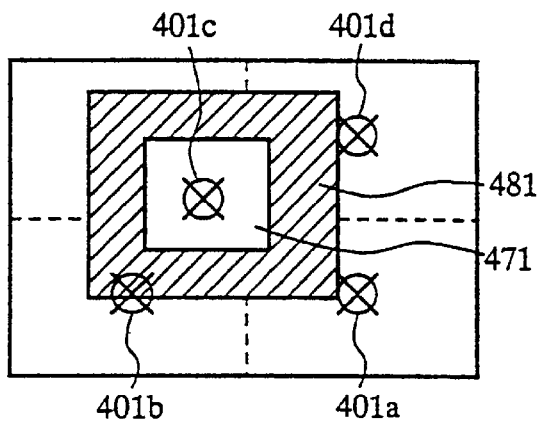
FIGS. 9(a), 9(b) and 9(c) are respectively diagrams depicting examples of position relationships between ranges to select the video cameras of the image capturing device of the medical support system shown in FIG. 1 and the video cameras.
Figure 9B:
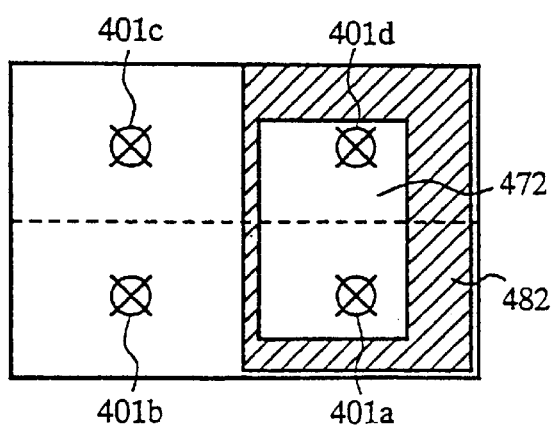
Figure 9C:
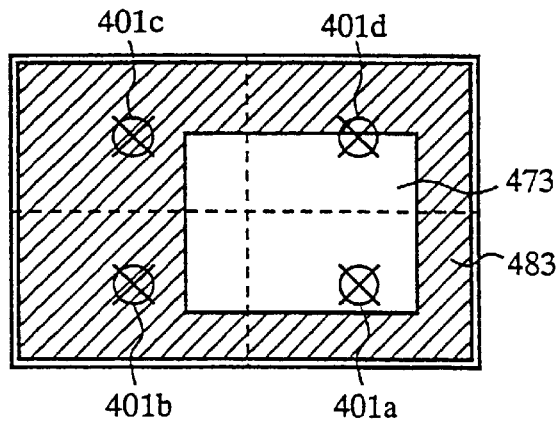

Next, when the range to be examined is selected through the displayed screen 6100, the camera position calculation unit 640 compares the selected range and the shooting ranges for the video cameras. If it is found that the selected range is smaller than the shooting range for one video camera, then the corresponding video camera kept at the closest distance from the position of gravity of the selected range is selected from the video cameras 401*a* through 401*d* and the selected video camera is shifted to the position of gravity of the selected range (see FIG. 9(*a*)). In FIG. 9(*a*), reference numerals 471 and 481 indicate a selected range and a shooting range for the video camera 401*c*.

If the selected range is larger than the shooting range of one video camera but smaller than a shooting range shootable by two video cameras, then the corresponding video cameras capable of performing shooting inclusive of the selected range are selected and take shooting at positions of defaults of these video cameras. In this case, the photographing is done by the two video cameras and the resultant images are merged into one. Thereafter, an image included in the selected range is cut out from the merged one and displayed (see FIG. 9(*b*)). In FIG. 9(*b*), reference numeral 472 indicates a selected range and reference numeral 482 indicates a combined shooting range of the video cameras 401*d* and 401*a*.

When the selected range does not correspond to any shooting range referred to above, all the video cameras 401*a* through 401*d* are selected and they perform photographing at shooting positions of defaults of the video cameras. Four images obtained after the photographing of the video cameras 401*a* through 401*d* are synthesized or combined into one and an image corresponding to the selected range is cut out from the composite image and displayed (see FIG. 9(*c*)). In FIG. 9(*c*), reference numeral 473 indicates a selected range and reference numeral 483 indicates a combined shooting range of the video cameras 401*a* through 401*d*.

Thus, since the video cameras 401*a* through 401 of the image capturing device 40 can be activated so as to satisfy the above-described restricted conditions, the time required before the photography is short and only the necessary image can be transferred and displayed with efficiency.

Figure 10:
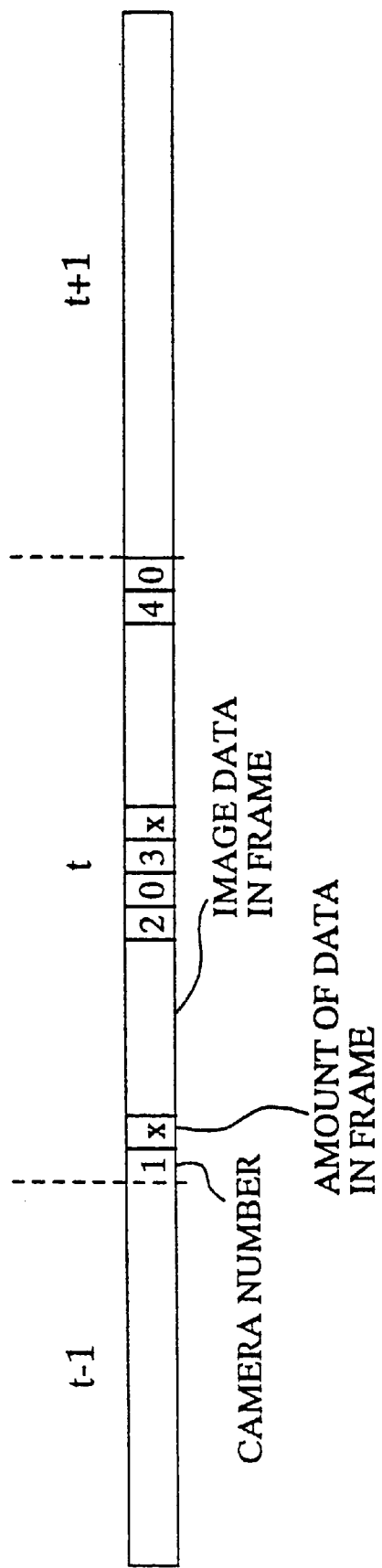
FIG. 10 is a diagram showing the structure of data used to transfer images obtained from the video cameras of the image capturing device of the medical support system shown in FIG. 1.

The pieces of patient's image information obtained from the image capturing device 40 are stored in both the information storage units 70 and 810 every shooting times. The image information are captured by the video cameras 401*a* through 401*d* every shooting times and serially transferred to the information storage units 70 and 810. FIG. 10 is a diagram for describing one example of a data format used to store/transfer the patient's image data. As shown in the drawing, the numbers for the respective cameras, the amounts of data in respective frames and image data in the frames at respective times t are stored in the information storage units 70 and 810.

The image mosaic generator 820 of the medical-side system 13 synthesizes a plurality of images obtained from a plurality of video cameras 401a through 401d, which are captured at the same shooting time, to produce one image high in resolution and wide in vision or visual field. The images obtained from the video cameras 401a through 401d of the image capturing device 40 are all identical in size to each other and covers a rectangular area including the whole body of a patient thereinside when these video cameras 401a through 401d take shooting at default positions. If a color correction or the like is made to images inherent in the video cameras 401a through 401d at this time, then the plurality of images captured at the same time provide less nonuniformity in image density because of the same illuminating condition. Therefore, a process for normalizing the color and density becomes easy.

Specific operations of the image mosaic generator 820 will next be explained.

The placement of images obtained from the video cameras 401a through 401d is determined from information about the positions of the vide cameras 401a through 401d. Next, mutual position fine adjustments are made to the images extending in the vertical and horizontal directions and an image registration process based on border lines is performed so that respective image frames are accurately spliced. Densities or colors of peripheral pixels located in the center lines of the respective images and in the vicinity of the center lines thereof are next subjected to a blending process.

Figure 11A:
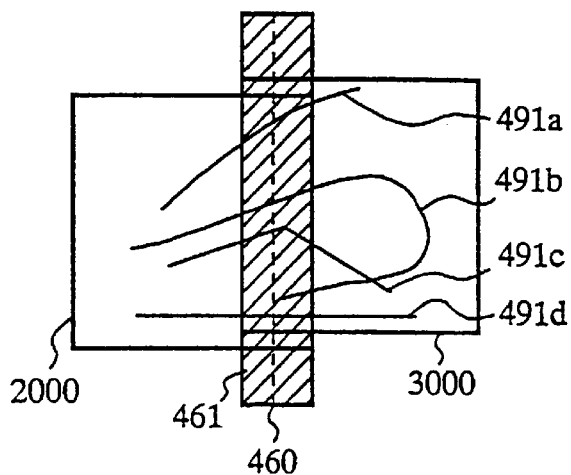
FIGS. 11(a), 11(b) and 11(c) are respectively diagrams for describing operations for splicing two images by the medical support system shown in FIG. 1.
Figure 11B:
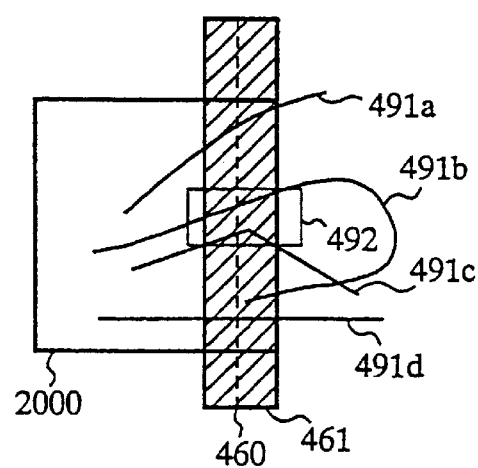
Figure 11C:
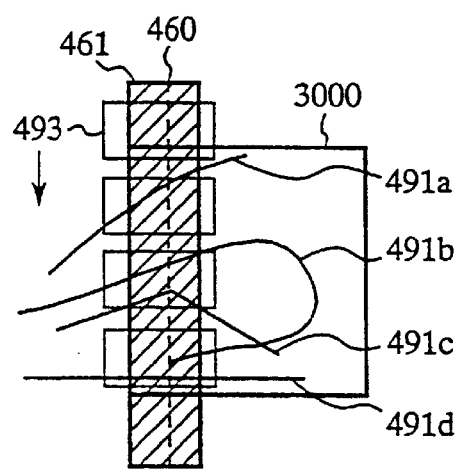

The specific operations of the image mosaic generator 820, for performing the image registration process based on the border lines will next be described with reference to FIGS. 11(*a*) through 11(*d*). A description will be made here of the case in which two images are combined together in the short-side direction. However, even in the case where the two images are combined together in the long-side direction, it can be implemented by the similar process. In order to extract border lines of the resultant two images 2000 and 3000, a process for extracting boundaries (where the thickness of each boundary is defined as greater than one pixel) is effected on the two images 2000 and 3000 using a boundary extraction filter called "image registration sobelfilter". Boundaries 491a, 491b, 491c and 491d are regarded as having been extracted as the boundaries here (see FIG. 11(*a*)).

Next, points where a center line 460 of an overlapping area 461 in which the shooting ranges of the video cameras overlap, intersects the boundary of the left-side image 2000, are determined. Further, a rectangular image having longitudinally-extending 20 to 40 pixels x transversely-extending area (equivalent to about the width of the overlapping area 461) is cut out at a location where the intersecting points reach the maximum. The cut image is regarded as a template image 492 (see FIG. 11(*b*)).

In the right-side image 3000, windows 493 each identical in size to the template image 492 are next moved along the center line 460 of the overlapping area 461 to make a comparison therebetween. A position (corresponding to, for example, a position where the difference in density or color reaches the minimum) at which the best matching is provided on both side of the center line, is found out. With the position as the reference, the original two images 2000 and 3000 are adjusted in position to precisely splice them.

Since the comparison is performed between the template image 492 small in size, which has been selected from the one image (corresponding to the image 2000 located on the left side here) and the image in the corresponding window 493 lying within the other image (corresponding to the image 3000 on the right side here) and identical in size to the template image 492, the time required to make the comparison is short. The closest spliced position can be obtained quickly and accurately in accordance with a two-dimensional template matching based on the commonly-used characteristic point recognition. Since it is unnecessary to recognize the characteristic points, an applicable image range becomes wide.

Figure 12:
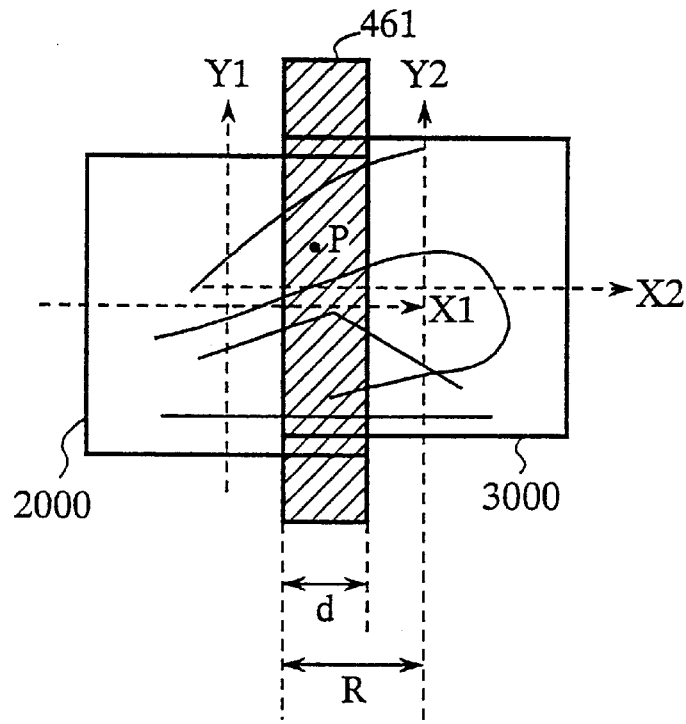
FIG. 12 is a diagram for describing an operation for splicing two images together by the medical support system shown in FIG. 1.

In the process for blending the densities of the center line 460 and the peripheral pixels located in the vicinity of the center line 460, the densities of the respective points in the overlapping area of the two images on the left and right sides are calculated from the following equations (1), (2) and (3):

$$I(p) = I1(p) \times s1(p) + I2(p) \times s2(p) \qquad (1)$$

$$s1(p) = -1.0 \times (x1 - R + d)/d + 1.0 \qquad (2)$$

$$s2(p) = 1.0 \times (x2 + R - d)/d + 1.0 \qquad (3)$$

where p indicates the position of each pixel that belongs to the overlapping area of the two images. As shown in FIG. 12, the position of p represented in the form of a coordinate system (X1-Y1 coordinate system) of an image 2000 on the left side as seen on the sheet, is given as (x1, y1), and the position of p represented in the form of a coordinate system (X2-Y2 coordinate system) of an image 3000 on the right side as seen on the sheet, is given as (x2, y2). I(p) indicates the value of a density of a pixel placed in the position at the point p of a composite image. I1(p) indicates the value of a density of a pixel placed in the position at the point p of the image 2000 on the left side. I2(p) indicates the value of a density of a pixel placed in the position at the point p of the image 3000 on the right side. R indicates the radius (corresponding to the shortest distance between the origin of a coordinate system and the boundary where the images are spliced) of an image area. d indicates the width of the overlapping area.

When the photographed patient's images are represented as white-and-black images, the blending process based on the aforementioned equations (1), (2) and (3) is effected thereon. Thus, a plurality of images can be smoothly spliced when the plurality of images are combined into one.

When the photographed patient's images are represented as colored images, tonal values of respective red, green and blue colors are calculated from the following equations:

$$R(p) = R1(p) \times s1(p) + R2(p) \times s2(p) \qquad (4)$$

$$G(p) = G1(p) \times s1(p) + G2(p) \times s2(p) \qquad (5)$$

$$B(p) = B1(p) \times s1(p) + B2(p) \times s2(p) \qquad (6)$$

where R(p), G(p) and B(p) respectively indicate tonal values of respective colors of R (red), G (green) and B (blue) of a pixel placed in a position at a point p of a composite image. R1(p), G1(p) and B1(p) respectively indicate tonal values of respective colors of R (red), G (green) and B (blue) of a pixel placed in the position at the point p of the image 2000 on the left side. R2(p), G2(p) and B2(p) respectively indicate tonal values of respective colors of R (red), G (green) and B (blue) of a pixel placed in the position at the point p of the image 3000 on the right side. R indicates the radius of an image area. d indicates the width of an overlapping area.

When the photographed patient's images are represented as the colored images, a blending process based on the aforementioned equations (4), (5) and (6) is executed. As a result, a plurality of images can be smoothly spliced upon synthesis of the images.

In the medical support system according to the first embodiment, the digital mosaic processor 800 of the medical-side system 13 synthesizes a plurality of images captured by the image capturing device 40 of the patient-side system 14 to produce and display an image indicative of the whole body of a patient. Therefore, a medical treater using the medical-side system 13 can effectively recognize the state of the patient body and precisely perform medical treatments or behaviors such as a diagnosis, instructions for medical treatment, etc. If the medical-side system 13 is provided with a display device for displaying an image of a patient's face thereon, a shooting device for shooting a doctor, a voice output device for outputting a patient's voice and a voice input device for inputting a doctor's voice and the patient-side system 14 is provided with a display device for displaying a doctor's picture thereon, a shooting device for photographing a patient, a voice output device for outputting the doctor's voice and a voice input device for inputting the patient's voice, and the doctor's voice and picture and the patient's voice and picture are bidirectionally transferred between the medical-side system 13 and the patient-side system 14, then the patient and the doctor can exchange information therebetween while they are mutually looking at their faces. Therefore, the patient can undergo medical treatments more comfortably and the medical treater can perform medical treatments more comfortably.

Second Embodiment

Figure 13B:
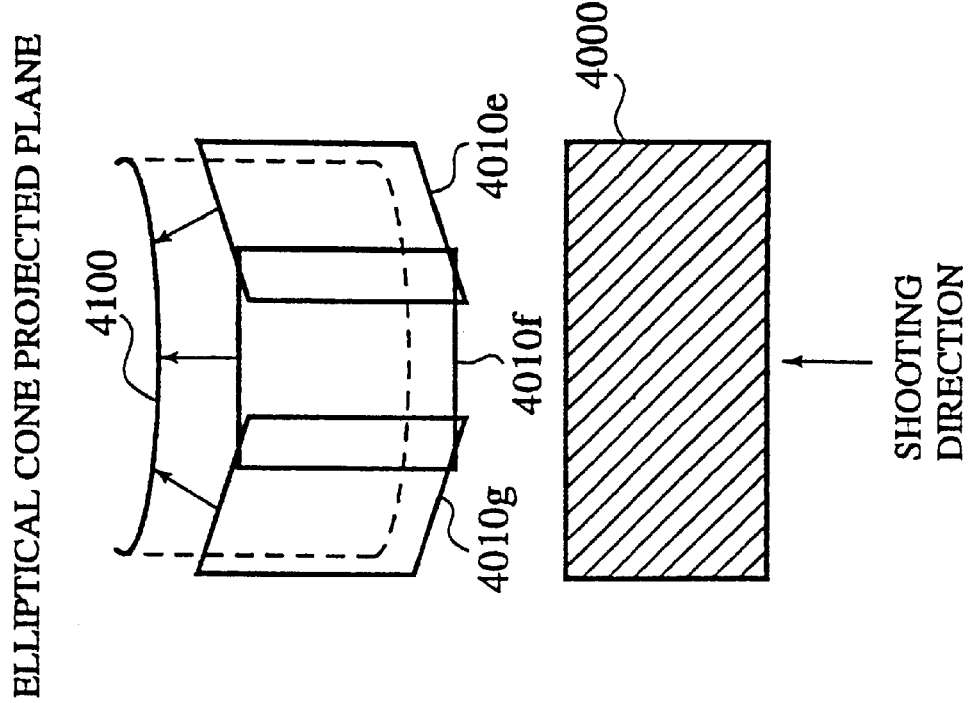
FIG. 13(b) is a diagram for describing the operation of the medical support system according to the second embodiment of the present invention.
Figure 13A:
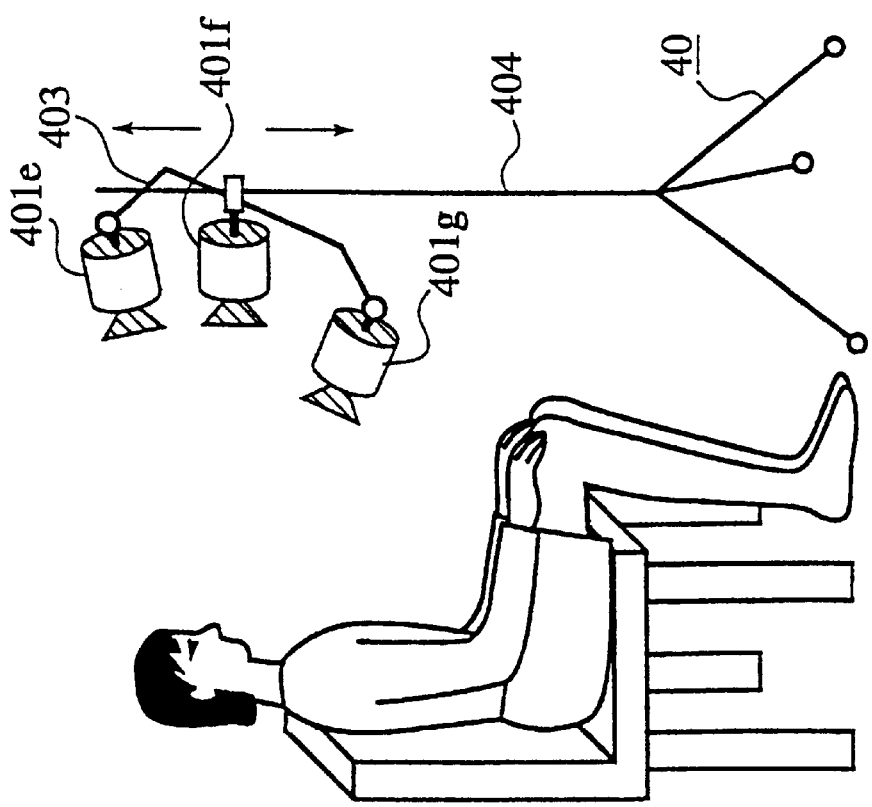
FIG. 13(a) is a diagram showing a configuration of an image capturing device of a medical support system according to a second embodiment (Second Embodiment) of the present invention.

FIG. 13(*a*) is a diagram showing one example of a specific configuration of an image capturing device 40 employed in a medical support system according to a second embodiment. In the drawing, reference numerals 401*e*, 401*f* and 401*g* indicate video cameras respectively. Reference numeral 403 indicates a holding member for holding the video cameras 401*e*, 401*f* and 401*g*. Reference numeral 404 indicates a support member for supporting the holding member 403. The holding member 403 is a bar-shaped bent member. Since the video cameras 401*e* through 401*g* are fixedly mounted to the holding member 403, they differ from each other in direction. The holding member 403 can make a change in its position along the support member 404 under the action of a drive means (not shown) (i.e., the video cameras 401*e* through 401*g* are activated so as to be able to move in upward and downward directions as seen on the sheet).

The image capturing device 40 employed in the second embodiment has predetermined angles formed in the shooting directions of the three video cameras 401*e* through 401*g*. As compared with the first embodiment in which all the video cameras take photographing from the same directions, information about patient's deep parts (e.g., information about the side of the patient) can be captured in the second embodiment.

In order to avoid geometrical distortions when three images captured by the image capturing device 40 employed in the second embodiment are combined together, it is necessary to first throw or project three image frames onto an elliptical cone plane 4100 tangent to three projected planes 4010*e*, 4010*f* and 4010*g* as shown in FIG. 13(*b*). Next, image registration and blending processes are performed on the elliptical cone projected plane 4100. Thereafter, the elliptical cone projected plane is projectively-transformed into a plane 4000 (corresponding to a plane orthogonal to the shooting direction of the video camera 401*f* in the present embodiment) orthogonal to its view direction. As a result, one wide image can be obtained. Thus, since the information about the images photographed from the multidirection can be combined together and displayed, a medical treater can recognize larger pieces of image information. Therefore, the medical treater can examine and diagnose the patient with efficiency.

Although ones identical in performance (shooting range, resolution) to each other have been used as the video cameras constituting the image capturing device in the first embodiment, video cameras different in performance from each other may be selectably configured. For example, an image low in time resolution in a wide visual field, which is obtained by combining together images photographed by a plurality of video cameras different in performance, and an image high in time resolution in a normal visual field, which is photographed by one video camera, are switched according to input information, so that a full-size figure and a part-size figure of a patient may be viewed according to suitable switching thereto.

Third Embodiment

Figure 14:
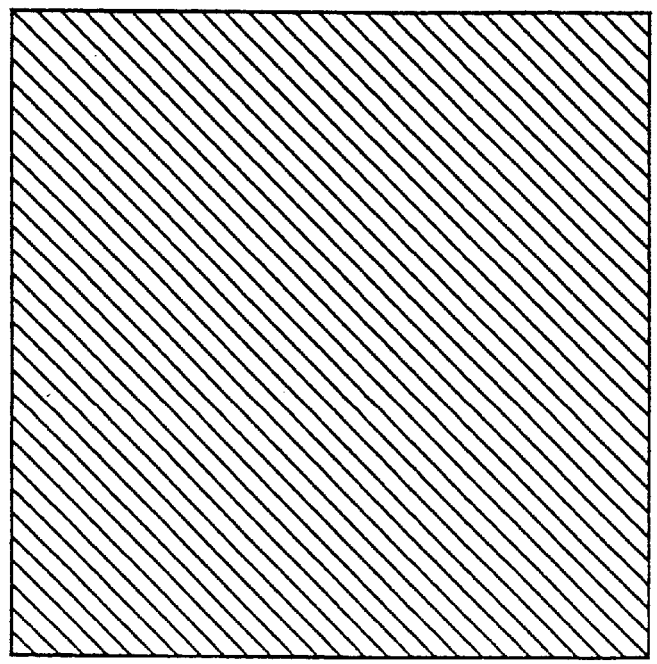
FIG. 14 is a diagram illustrating one example of a background pattern employed in a medical support system according to a third embodiment (Third Embodiment) of the present invention.

A medical support system according to a third embodiment is characterized in that when patient's images are shot, an image for the background thereof is patterned as a figure. When patient's images are photographed with a diagonally-shaded pattern as a background as shown in FIG. 14 by way of example, a plurality of images can be spliced together using image information about the background pattern upon splicing the images by an image mosaic processor, so that the images can be spliced accurately. Particularly if a pattern with a diagonally-shaded background is regarded as a background image, then the boundaries of images respectively photographed by video cameras do no overlap with the background pattern. Therefore, the images can be accurately spliced together without loss of information about the background pattern.

Figure 15A:
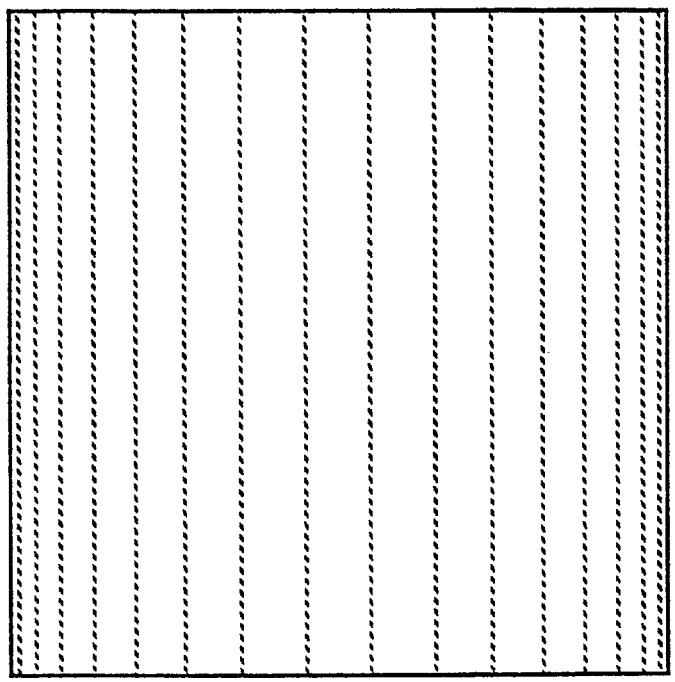
FIGS. 15(a) and 15(b) are respectively diagrams showing other examples of background patterns employed in the medical support system shown in FIG. 14.
Figure 15B:
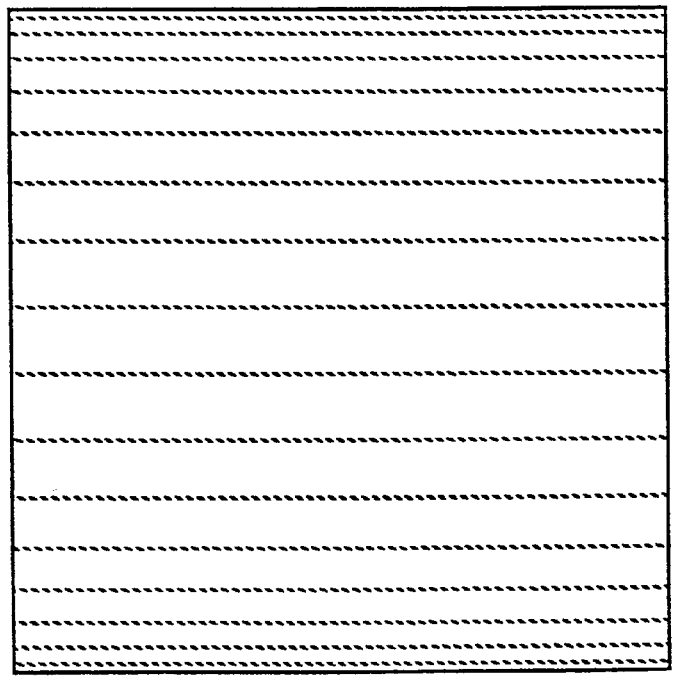
Figure 16A:
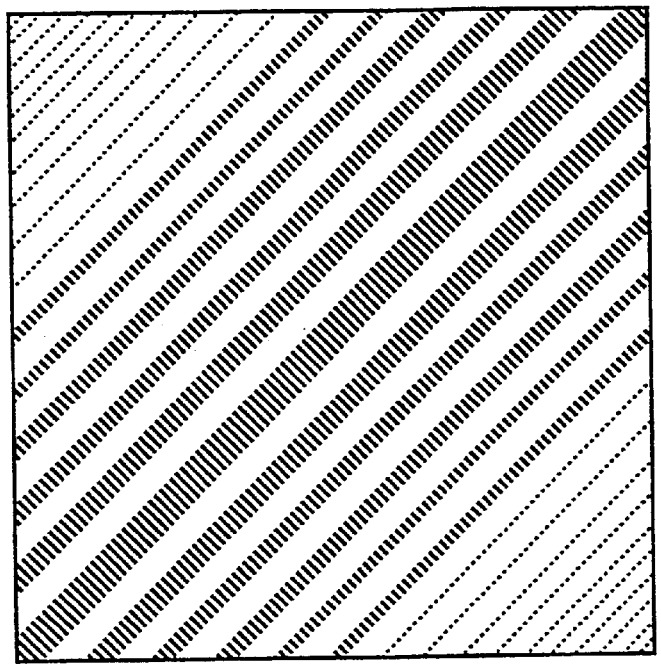
FIGS. 16(a) and 16(b) are respectively diagrams illustrating further examples of background patterns employed in the medical support system shown in FIG. 14.
Figure 16B:
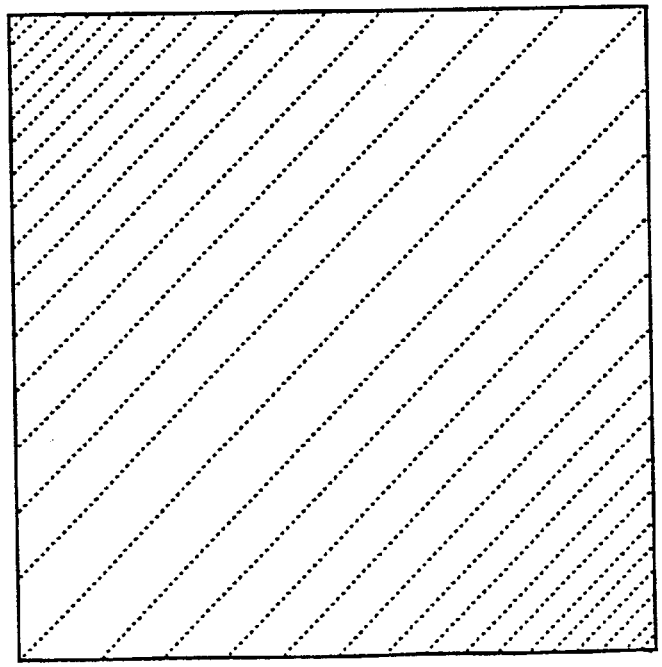
Figure 17:
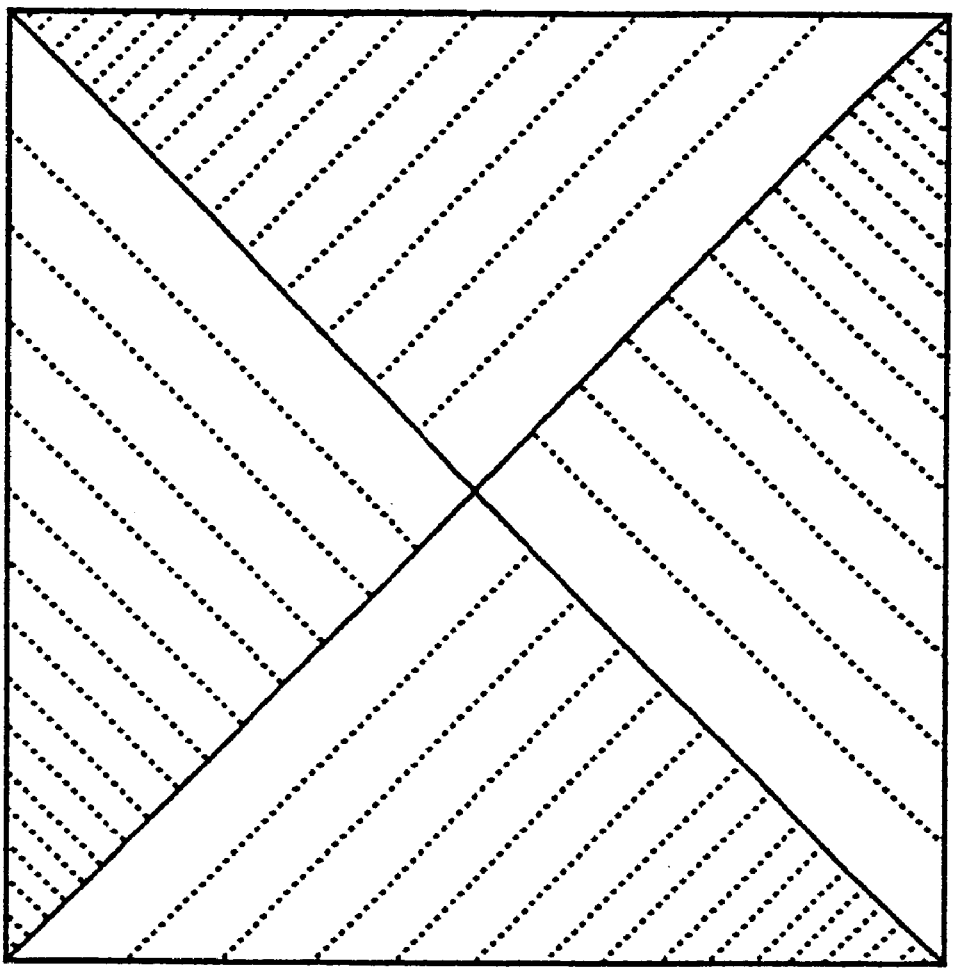
FIG. 17 is a diagram depicting a still further example of a background pattern employed in the medical support system shown in FIG. 14.

Alternatively, the background pattern may include one obtained by varying the thicknesses of lines along a predetermined direction (see FIG. 16(*a*)), ones obtained by varying the distances between adjacent lines along predetermined directions (see FIGS. 15(*a*), 15(*b*) and 16(*b*)), one obtained by dividing a background into a plurality of blocks and forming patterns every blocks (see FIG. 17), one subjected to a gradation process along a predetermined direction (not shown), etc.

Only when a plurality of images cannot be spliced together satisfactorily in the case of only images for a patient's body, a process for splicing the images using information about these background images may be performed.

While the preferred embodiments of the present invention have been described above, the description of these is illustrated ones. It should be understood that modifications and changes from these description can be made without departing from the spirit and scope of the following claims.

What is claimed is:

1. A medical support system comprising:
   a patient-side system including patient image shooting means comprising a plurality of shooting devices for photographing a patient's body and forming a plurality of images, respective images displaying respective parts of the patient's body;
   a medical-side system located at a position spaced away from said patient-side system and including image synthesizing means for splicing together, at boundary portions, respective adjacent images of parts of the patient's body to produce a composite image displaying an area of the patient's body extending across the respective adjacent images, and display means for displaying the composite image produced by said image synthesizing means; and communication means for transmitting information between said medical-side system and said patient-side system and for transferring the plurality of images produced by said patient image shooting means to said medical-side system.

2. The medical support system according to claim 1, wherein said medical-side system has shooting-device position control means for controlling the positions of the plurality of shooting devices of said patient image shooting means in said patient-side system.

3. The medical support system according to claim 2, wherein said medical-side system has shooting-device position display means for displaying the positions of said plurality of shooting devices thereon.

4. The medical support system according to claim 2, wherein said medical-side system has selecting means for selecting a patient part/range photographed by said patient-side system and said shooting-device position control means controls said patient image shooting means according to the information selected by said selecting means.

5. The medical support system according to claim 4, wherein said medical-side system has human-body form image display means for displaying a human-body form image corresponding to the form of a human body and displaying a part of the human-body form image corresponding to the patient part selected by said selecting means in distinction from other parts.

6. The medical support system according to claim 5, wherein said medical-side system has shot-state input means for selecting and inputting a photographed posture of the patient and said human-body form image display means displays thereon a human-body form image corresponding to the posture inputted to said shot-state input means.

7. The medical support system according to claim 1, wherein said medical-side system includes voice input means for inputting a voice, voice output means for outputting voice information sent from said patient-side system and shooting means for photographing images, and said patient-side system includes display means for displaying the images obtained by the shooting means of said medical-side system and voice output means for outputting the voice inputted from the voice input means of said medical-side system.

8. The medical support system according to claim 7, wherein said medical-side system has voice information recognizing means for recognizing information about the voice inputted from said voice input means and outputting a signal for specifying a human body part to be photographed.

9. The medical support system according to claim 1, wherein said plurality of shooting devices of said patient-side system are located in a common plane.

10. The medical support system according to claim 9, wherein said plurality of shooting devices are movable within the plane.

11. The medical support system according to claim 1, wherein said plurality of shooting devices differ from each other in shooting directions.

12. The medical support system according to claim 1, wherein said medical-side system has shooting-device position calculating means for calculating the position of each shooting device of said patient-side system, said shooting-device position calculating means calculating the positions of said plurality of shooting devices so that movements of said plurality of shooting devices reach minimum or said plurality of shooting devices reaches a minimum quantity.

13. The medical support system according to claim 1, wherein said patient-side system has first information storing means for storing the images produced by said patient image shooting means and said medical-side system has second information storing means for storing the images sent from said patient-side system.

14. The medical support system according to claim 1, wherein:

said image synthesizing means includes means for determining a layout of the plurality of images from information about positions of the plurality of shooting devices, boundary extracting means for extracting boundaries of the plurality of images through a boundary extracting filter, means for calculating a center line of an overlapping area in which respective adjacent images overlap each other in vicinities of the boundaries of respective images, means for calculating intersections of the boundaries extracted from the boundary extracting means of the adjacent images and extracting an area in which the intersections increase, thereby producing a template image, means for creating a window identical in size to the template image and calculating a position used to splice the adjacent images together while moving the window within the overlapping area, registration processing means for adjusting a mutually related position of the adjacent images in a vertical or horizontal direction and effecting a registration process on the adjacent images so that the boundaries of the adjacent images are joined to each other, and intensity blending process executing means for effecting a blending process of at least one of intensities and color tones of the center line and pixels around the center line.

15. The medical support system according to claim 14, wherein said intensity blending process executing means calculates densities of respective pixels within the overlapping area from the following equations (1) through (3):

$$I(p) = I1(p) \times s1(p) + I2(p) \times s2(p) \qquad (1)$$

$$s1(p) = -1.0 \times (x1 - R + d)/d + 1.0 \qquad (2)$$

$$s2(p) = 1.0 \times (x2 + R - d)/d + 1.0 \qquad (3)$$

where p: the position of each pixel that belongs to the overlapping area, wherein the position of p represented in the form of a coordinate system of one image is given as (x1, y1) and the position of p represented in the form of a coordinate system of the other image is given as (x2, y2), I(p): the density of a pixel at the point p of a composite image, I1(p): the density of a pixel at the point p of one image, I2(p): the density of a pixel at the point p of the other image, R: the radius of an image area, and d: the width of the overlapping area.

16. The medical support system according to claim 14, wherein said means for effecting a blending process calculates densities of respective pixels within the overlapping area from the following equations (4) through (8):

$$R(p) = R1(p) \times s1(p) + R2(p) \times s2(p) \quad (4)$$

$$G(p) = G1(p) \times s1(p) + G2(p) \times s2(p) \quad (5)$$

$$B(p) = B1(p) \times s1(p) + B2(p) \times s2(p) \quad (6)$$

$$s1(p) = -1.0 \times (x1 - R + d)/d + 1.0 \quad (7)$$

$$s2(p) = 1.0 \times (x2 + R - d)/d + 1.0 \quad (8)$$

where p: the position of each pixel that belongs to the overlapping area, wherein the position of p represented in the form of a coordinate system of one image is given as (x1, y1) and the position of p represented in the form of a coordinate system of the other image is given as (x2, y2), R(p), G(p) and B(p): tonal values of respective colors of R (red), G (green) and B (blue) of a pixel at a point p of a composite image, R1(p), G1(p) and B1(p): tonal values of respective colors of R (red), G (green) and B (blue) of a pixel at the point p of one image, R2(p), G2(p) and B2(p): tonal values of respective colors of R (red), G (green) and B (blue) of a pixel at the point p of the other image, R: the radius of an image area, and d: the width of the overlapping area.

17. The medical support system according to claim 1, wherein a background pattern is provided and said plurality of shooting devices photographs the patients body with the background pattern as background.

18. The medical support system according to claim 17, wherein the background pattern includes straight lines.

19. The medical support system according to claim 18, wherein the straight lines have varying widths.

20. The medical support system according to claim 18, wherein spaces between adjacent pairs of the straight lines vary.

* * * * *